United States Patent [19]

Rochat et al.

[11] Patent Number: 4,760,151
[45] Date of Patent: Jul. 26, 1988

[54] DITHIOKETO PYRROLOPYRROLES

[75] Inventors: Alain C. Rochat, Fribourg; Abul Iqbal, Ettingen; Rémy Jeanneret, Allschwil; Jin Mizuguchi, Marly, all of Switzerland

[73] Assignee: Ciba-Geigy Corporation, Ardsley, N.Y.

[21] Appl. No.: 901,864

[22] Filed: Aug. 29, 1986

Related U.S. Application Data

[62] Division of Ser. No. 815,327, Dec. 31, 1985, Pat. No. 4,632,893.

[30] Foreign Application Priority Data

Jan. 3, 1985 [CH] Switzerland ............... 14/85

[51] Int. Cl.$^4$ ............... C07D 401/14; C07D 487/04
[52] U.S. Cl. ............... 548/453; 546/271
[58] Field of Search ............... 548/453; 546/271

[56] References Cited

U.S. PATENT DOCUMENTS 4,579,949 4/1986 Rochat et al. ............... 548/453

Primary Examiner—Glennon H. Hollrah
Assistant Examiner—D. B. Springer
Attorney, Agent, or Firm—Luther A. R. Hall

[57] ABSTRACT

Compounds of formula (1)

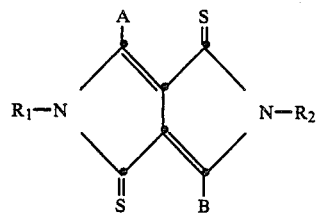

wherein A and B are identical or different alkyl, aralkyl or cycloalkyl groups or carbocyclic or heterocyclic aromatic radicals, $R_1$ and $R_2$ are hydrogen atoms or substituents which do not impart solubility in water, are particularly suitable as photoconductive substances.

4 Claims, No Drawings

DITHIOKETO PYRROLOPYRROLES

This is a divisional of application Ser. No. 815,327, filed on Dec. 31, 1985, now U.S. Pat. No. 4,632,893, issued on Dec. 30, 1986.

The invention relates to novel pyrrolopyrroles of formula (1)

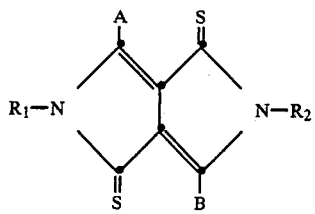

wherein A and B are identical or different alkyl, aralkyl or cycloalkyl groups or carbocyclic or heterocyclic aromatic radicals, $R_1$ and $R_2$ are hydrogen atoms or substituents which do not impart solubility in water.

A and B in formula (1) as alkyl groups may be branched, unbranched, saturated or unsaturated, and contain preferably 1 to 18, most preferably 1 to 12, carbon atoms, e.g. methyl, ethyl, n-propyl, isopropyl, n-butyl, sec-butyl, tert-butyl, tert-amyl, n-pentyl, n-hexyl, 1,1,3,3-tetramethylbutyl, n-heptyl, n-octyl, nonyl, decyl, undecyl, dodecyl or stearyl.

A and B are aralkyl groups are preferably those which contain a preferably mono- to tricyclic, most preferably mono- or bicyclic, aryl radical which is attached through a branched or unbranched alkyl or alkenyl group containing 1 to 12, preferably 1 to 6 and most preferably 1 to 4, carbon atoms. Examples of such aralkyl groups are benzyl and phenylethyl.

A and B as isocyclic aromatic radicals are preferably mono- to tetracyclic, most preferably mono- or bicyclic, radicals, e.g. phenyl, diphenyl or naphthyl radicals. A and B as heterocyclic aromatic radicals are preferably mono- to tricyclic radicals. Said radicals may be purely heterocyclic or may contain a heterocyclic ring and one or more fused benzene rings, e.g. pyridyl, pyrimidyl, pyrazinyl, triazinyl, furanyl, pyrrolyl, thiophenyl, quinolyl, coumarinyl, benzofuranyl, benzimidazolyl, benzoxazolyl, dibenzofuranyl, benzothiophenyl, dibenzothiophenyl, indolyl, carbazolyl, pyrazolyl, imidazolyl, oxazolyl, isooxazolyl, thiazolyl, indazolyl, benzothiazolyl, pyridazinyl, cinnolyl, quinazolyl, quinoxalyl, phthalazinyl, phthalazinedionyl, phthalimidyl, chromonyl, naphtholactamyl, benzopyridonyl, maleinimidyl, naphtharidinyl, benzimidazolonyl, benzoxazolonyl, benzothiazolonyl, benzothiazolinyl, quinazolonyl, pyrimidyl, quinoxalonyl, phthalazonyl, dioxapyrimidinyl, pyridonyl, isoquinolonyl, isoquinolinyl, isothiazolyl, benzisoxazolyl, benzisothiazolyl, indazolonyl, acridinyl, acridonyl, quinazolinedionyl, quinoxalinedionyl, benzoxazinedionyl and naphthalimidyl. Both the isocyclic and the heterocyclic aromatic radicals may contain the conventional substituents as cited for example in European published application No. 94 911.

$R_1$ and $R_2$ in formula (1) as substituents which do not impart solubility in water are for example branched or unbranched, saturated or unsaturated alkyl groups containing preferably 1 to 18, most preferably 1 to 12, carbon atoms. These groups may be unsubstituted or substituted by hydroxy, halogen, alkoxy, acyloxy, alkylmercapto, alkoxycarbonyl or cyano. Examples of such groups are methyl, ethyl, n-propyl, isopropyl, n-butyl, sec-butyl, tert-butyl, tert-amyl, n-pentyl, n-hexyl, allyl, hydroxyethyl, 1,1,3,3-tetramethylbutyl, n-heptyl, n-octyl, nonyl, decyl, undecyl, dodecyl, stearyl, hydroxymethyl, trifluoromethyl, trifluoroethyl, cyanoethyl, methoxycarbonylmethyl or acetoxymethyl.

$R^1$ and $R^2$ may also be aryl groups, preferably unsubstituted phenyl or phenyl substituted by halogen, $C_1$-$C_{12}$alkyl, $C_1$-$C_{12}$alkoxy, $C_1$-$C_{12}$alkylmercapto, trifluoromethyl or nitro. Those compounds of formula (1) wherein $R_1$ and $R_2$ are hydrogen are of particular interest. Likewise preferred are those compounds of formula (1) wherein A and B are identical or different radicals of formula (2)

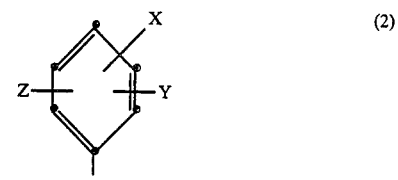

wherein each of X, Y and Z independently is a hydrogen or halogen atom, trifluoromethyl, cyano, $C_1$-$C_{12}$alkyl, $C_1$-$C_{12}$alkoxy, $C_1$-$C_{12}$-alkylmercapto, $C_2$-$C_6$alkoxycarbonyl or $C_2$-$C_6$dialkylamino group, or is a phenoxy, phenylmercapto or phenoxycarbonyl group, each of which is unsubstituted or substituted by halogen, $C_1$-$C_6$alkyl or $C_1$-$C_6$-alkoxy, at least one of the substituents X, Y and Z being a hydrogen atom. The substituents X, Y and Z are for example in ortho-, meta- or para-position, preferably in meta- or para-position, to the dithioketopyrrolopyrrole group.

Particularly preferred compounds of formula (1) are those wherein A and B are identical or different radicals of formula (3)

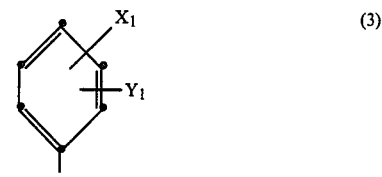

wherein one of the substituents $X_1$ and $Y_1$ is a hydrogen, chlorine or bromine atom, a methyl, cyano, N,N-dimethylamino, N,N-diethylamino, $C_1$-$C_{12}$alkoxy, $C_1$-$C_{12}$alkylmercapto or $C_2$-$C_4$alkoxycarbonyl group, and the other substitutent is a hydrogen atom. $X_1$ and $Y_1$ are for example in ortho-, meta- or para-position, preferably in meta- or para-position, to the dithioketopyrrolopyrrole group.

The compounds of formula (1) are obtained for example by heating a diketopyrrolopyrrole of formula (4)

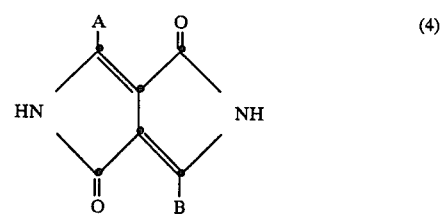

wherein A and B are as defined above, with a thionating agent. Suitable thionating agents are the known ones such as tetraphosphorus trisulfide (P$_4$S$_3$), tetraphosphorus heptasulfide (P$_4$S$_7$), tetraphosphorus decasulfide (P$_4$S$_{10}$) and its pyridine complex P$_4$S$_{10}$.4C$_5$H$_5$N, as well as dithiaphosphetanes, in particular 2,4-bis-(4-methoxyphenyl)-1,3-dithia-2,4-diphosphetane 2,4-disulfide (Lawesson's reagent), with the last-named compound and tetraphosphorus decasulfide being preferred. The reaction is conveniently carried out at temperature in the range from 50° to 250° C. with an excess of the thionating agent, preferably in the range from 80° to 150° C. in an inert solvent. Suitable solvents are for example aromatic hydrocarbons such as benzene, toluene, xylene or tetrahydronaphthalene; chlorinated aromatic hydrocarbons such as chlorobenzene and o-dichlorobenzene; ethers such as dimethoxy ether, diethylene glycol dimethyl ether, anisole, dioxane or diphenyl ether; or also nitriles such as acetonitrile or benzonitrile; or amides or thioamides such as dimethylthioformamide, dimethylthioacetamide, tetraethylsulfamide and hexamethylphosphoric triamide; or mixtures of the above solvents.

The resultant dithioketopyrrolopyrroles can usually be isolated by filtration. Depending on the use, aftertreatment is necessary to increase the chemical purity (e.g. recrystallisation, sublimation etc.) and/or to modify the crystal form (e.g. conditioning in an organic solvent). The following solvents are particularly suitable for this purpose: benzenes substituted by halogen atoms or by alkyl or nitro groups, e.g. xylenes, chlorobenzene, o-dichlorobenzene or nitrobenzene; as well as pyridine bases such as pyridine, picoline or quinoline; and also ketones such as acetone, methyl ethyl ketone or cyclohexanone; ethers such as ethylene glycol monomethyl ether, ethylene glycol monoethyl ether or tetrahydrofuran; amides such as dimethylformamide or N-methylpyrrolidone; alcohols such as methanol or ethanol; as well as dimethyl sulfoxide, sulfolane, acetonitrile, benzonitrile, methyl acetate and ethyl acetate. Preferred solvents are acetone, tetrahydrofuran, dimethylformamide, methanol, dimethyl sulfoxide, ethyl acetate and acetonitrile.

Depending on the nature of the radicals A, B, R$_1$ and R$_2$ and of the polymers to be coloured, the compounds of formula (1) may be used as polymer-soluble dyes or as pigments.

The compounds of formula (1) are of particular interest as photoconductive substances, for example in electrophotographic recording materials. Such materials consist of a conductive support and a layered structure which insulates in the dark, but which is conductive when subjected to exposure. This layered structure may consist of one or more layers. If it consists of a single layer, then at least one photoconductive substance is dispersed in at least one binder or is vaporised directly onto a conductive support. A multilayered structure consists of at least one charge-carrier generating layer, containing one or more photoconductive substances, and of at least one charge transporting layer.

Accordingly, a further embodiment of the present invention is electrophotographic recording material consisting of at least one conductive support, one layer which when subjected to exposure generates charges and one charge transporting layer, with at least one of said layers containing at least one compound of formula (1).

The conductive support may consist of a metal plate or sheet which is either rough or has been pretreated e.g. by buffing and which consists e.g. of aluminium, zinc, magnesium, copper or an alloy of these metals. In the case of aluminium, the pretreatment may consist in anodisation. Plastic sheets which have been vapour-blasted with aluminium, as well as polymer films with a metallised surface, are also suitable supports.

The layered structure contains the dithioketopyrrolopyrroles as substances which when subjected to exposure generate charges, which substances act together with the charge transporting substances present in said layered structure. Such a layered structure makes it possible, after previous static charging and imagewise exposure, to produce a corresponding pattern of charged and discharged areas (latent image) which can be converted by known reprographic methods into a visible image.

Exposure can be effected with light in the visible wave range. However, a particular advantage of the dithioketopyrrolopyrroles is that they are also capable of absorbing rays in the near infrared range and that they are also photoconductive in this wave length range. The range of 700 to 900 nm in which the high-energy gallium arsenide laser operates is of particular interest.

On account of the fact that they exhibit high dark resistance, the dithioketopyrrolopyrroles help to maintain static potential in unexposed areas.

If the layered structure consists of a single layer, then this contains one or more dithioketopyrrolopyrroles in finely dispersed form, optionally together with charge transporting substances, in an organic binder. The binder is film forming, insulating and adhesive. Depending on the application, the binder is soluble in organic solvents or in basic mixtures of organic solvents which may also contain water. Particularly suitable binders are those based on polycondensation and polyaddition products such as polyamides, polyurethanes, polyesters, epoxy resins, phenoxy resins, polyketones, polycarbonates, polyvinyl ketones, polystyrenes, polyvinyl carbazoles, polyacrylamides, polymethyl methacrylates, polyvinyl butyrates, polyvinyl chlorides, as well as copolymers such as styrene/maleic anhydride copolymers or styrene/methacrylic acid/methacrylate copolymers.

If the layered structure consists of more than one layer, then the double layer is the focus of interest. In such a case, first a charge generating layer is applied to the conductive support and then a charge transporting layer is applied to the first layer. The layers may also be applied in reverse order. One of the layers, preferably the charge generating layer, contains at least one dithioketopyrrolopyrrole. This may be dissolved or finely dispersed in an organic binder. Application onto the conductive layer is effected for example by coating it with a solution or dispersion of the binder/pigment mixture in an organic solvent and subsequently evaporating off the solvent. The dithioketopyrrolopyrroles may, however, also be vaporised onto the conductive support.

The second layer contains one or more charge transporting substances which are preferably dissolved or dispersed in an organic solvent. Suitable charge transporting substances are a variety of aromatic, preferably nitrogen-containing compounds such as hydrazones or aromatic amines which may contain alkylidene bridges or radicals. Examples of such substances are those described in German Offenlegungsschrift No. 34 47 685, pp. 57–65.

Although the pigments of the present invention have a final absorption of up to 780 nm, they are insufficiently photoconductive for laser recording. However, a method as now been found which makes it possible to shift this absorption considerably to higher wave lengths. This is achieved by exposing the above-described resultant photographic recording materials to solvent vapour, e.g. acetone, tetrahydrofuran, dimethylformamide, methanol, acetonitrile, dimethyl sulfoxide or ethyl acetate vapour, for 1 to 2 hours.

This method of shifting the wave length is known with regard to specific phthalocyanines from the publication of K. Arishima et al., Appl. Phys. Letters 40 (3), p. 279 (1982). In this case, a shifting to longer wave lengths of about 90 nm is achieved. Attempts were therefore made to apply this method to 1,4-diketopyrrolo[3,4-c]pyrroles; however, the outcome was a shifting to shorter wave lengths. Surprisingly, the application of this method to materials containing the dithioketopyrrolopyrroles of the present invention resulted in a quite unexpected shifting to longer wave lengths of about 130 nm and more. This solvent treatment also causes an increase of about 100 units in the dark resistance and the photoconductivity.

The same spectral shifting, as well as similar values for the dark resistance and the photoelectric current, are also obtained with the powdered pigments; these pigments are first ground, then treated with a solvent, e.g. ethyl acetate, and subsequently applied with a binder to a support.

Accordingly, a further embodiment of the invention is the preparation of electrophotographic recording material, which comprises applying a compound of formula (1) with binders to a conductive support or vaporising said compound in vacuo onto said support, treating the layer thus prepared with an organic solvent in the liquid or gaseous state, and subsequently adding a second layer containing an aromatic, nitrogen-containing compound.

In order to improve the physical properties thereof, the charge generating and charge transporting layers may also contain additives, such as levelling agents, surface-active agents or plasticisers.

The invention is illustrated by the following Examples:

EXAMPLE 1

Under nitrogen, a 200 ml sulfonating flask equipped with propeller mixer, thermometer and reflux condenser is charged with 2.89 g of 1,4-diketo-3,6-diphenyl-pyrrolo[3,4-c]pyrrole and 4.95 g of 2,4-bis(4-methoxyphenyl)-1,3-dithia-2,4-diphosphetane 2,4-disulfide (Lawesson's reagent), and these compounds are then covered with 60 ml of xylene mixture and 2.5 ml of hexamethylphosphoric triamide. The mixture is stirred vigorously and then heated under reflux at 133° C. After boiling for 7 hours, the mixture is cooled to about 90° C. The resultant product is isolated by filtration, washed with warm xylene, then with a small amount of acetone and finally with methanol and dried in vacuo at 90° C., affording 3.04 g of the compound of the formula

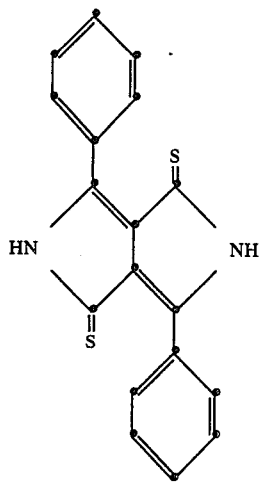

as blackish blue crystalline powder.

Analysis: C=65.73%; N=7.88%; H=4.00%; S=17.2%. Melting point above 350° C. with decomposition In accordance with MS, NMR and elementary analysis this corresponds to the following empirical formula

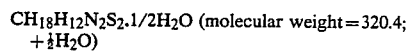

$CH_{18}H_{12}N_2S_2.1/2H_2O$ (molecular weight=320.4; +½$H_2O$)

In order to obtain a particularly pure product, the crude product can be recrystallised preferably from dimethyl sulfoxide and finally, after filtration, be conditioned in methanol in conventional manner.

EXAMPLE 2

Under nitrogen, a 200 ml sulfonating flask equipped with propeller mixer, thermometer and reflux condenser is charged with 2.21 g of 1,4-diketo-3,6-di(p-tolyl)pyrrolo[3,4-c]pyrrole and 3.47 g of Lawesson's reagent, and these compounds are then covered with 70 ml of xylene mixture and 2.0 ml of hexamethylphosphoric triamide. The mixture is stirred vigorously and then heated under reflux at 132° C. Since the mixture becomes considerably thicker, it has to be diluted with 10 ml of xylene mixture. After boiling under reflux for 12 hours, the reaction mixture is cooled to about 80° C. The resultant product is isolated by filtration, washed in succession with xylene mixture and methanol and then dried in vacuo at 100° C., affording 1.47 g of the compound of the formula

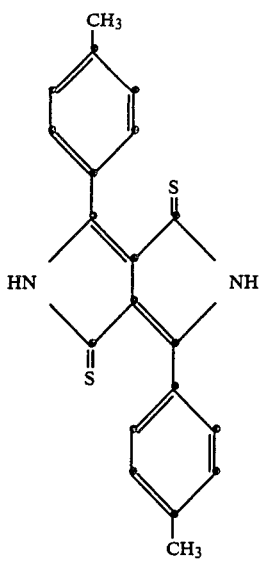

as dark blue powder.

Analysis: C=68.06%; N=7.71%; H=4.76%; S=16.86%; Melting point above 350° C. with decomposition In accordance with MS, NMR and elementary analysis this novel crude product is of the following empirical formula $C_{20}H_{16}N_2S_2$ with small amount of water (molecular weight=348.3+a small amount of water)

EXAMPLE 3

Under nitrogen, a 100 ml of sulfonating flask equipped with propeller stirrer, thermometer and reflux condenser is charged, free from water, with 1.14 g of 1,4-diketo-3-phenyl-6-(3,4,5-trimethoxyphenyl)pyrrolo[3,4-c]pyrrole, 1.48 g of Lawesson's reagent and 50 ml of xylene mixture. The suspension is heated under reflux and, with vigorous stirring, is kept under reflux at 131° C. for 1 hour. The reaction mixture is then cooled to 80° C. and filtered with suction. The insoluble pigment is thoroughly washed first with xylene and then with methanol. Drying is effected at 70°–80° C. in a vacuum furnace. The yield is 1.29 g of the compound of the formula

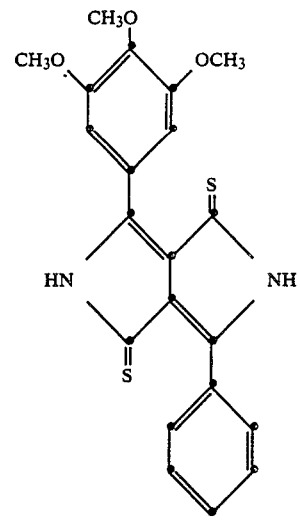

as blackish blue powder.

Melting point: 280°–285° C. (decomp.). The structure is confirmed by NMR analysis.

EXAMPLE 4

Under nitrogen, a 100 ml sulfonating flask equipped with propeller mixer, thermometer and reflux condenser is charged, free from water, with 0.95 g of N,N'-dimethyl-1,4-diketo-3,6-diphenylpyrrolo[3,4-c]pyrrole, 1.22 g of Lawesson's reagent (ex Fluka) and 50 ml of toluene. The mixture is stirred vigorously, heated to gentle reflux (about 102° C.) and kept at this temperature for 1½ hours. The mixture is subsequently cooled to 50° C., diluted with 50 ml of methanol, stirred for 30 minutes at about 50° C. and then allowed to cool to room temperature. The precipitated blue crystals are isolated by filtration, washed with methanol and dried at 70°–80° C. The yield is 0.76 g of crude product. Recrystallisation in xylene affords 0.64 g of pure compound of the formula

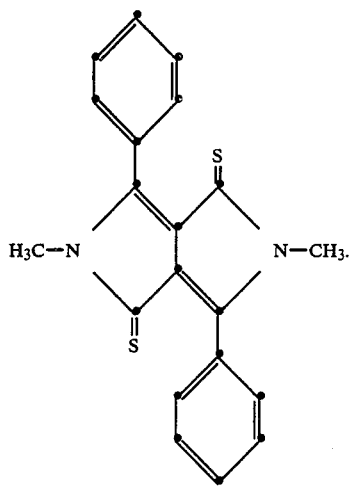

Analysis: C=68.76%; N=8.03%; H=4.69%; S=18.22%. Melting point: 256°–260° C.

EXAMPLE 5

1.74 g of 1,4-diketo-3,6-di(4-methoxyphenyl)pyrrolo[3,4-c]pyrrole and 2.48 g of Lawesson's reagent are reacted in exact accordance with the procedure of Example 2. No additional dilution is necessary. After drying, 1.83 g of the compound of the formula

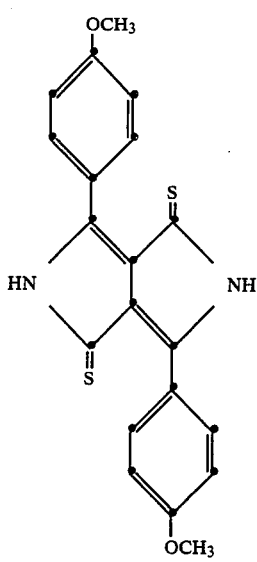

are obtained as dark blue powder.

Analysis: C=62.9%; N=7.25%; H=4.35%; S=16.2%. Melting point above 350° C. with decomposition The structure of the pigment is confirmed by spectroscopic data (IR, NMR and MS).

EXAMPLE 6

Under nitrogen, a 100 ml sulfonating flask equipped with propeller mixer, thermometer and reflux condenser is charged with 1.38 g of 1,4-diketo-3,6-bis(4-dodecylmercaptophenyl)pyrrolo[3,4-c]pyrrole, 0.99 g of Lawesson's reagent and 30 ml of xylene mixture. The mixture is heated to 130° C. and kept at this temperature for 2 hours. The reaction mixture is subsequently cooled to 80° C. The product is isolated by filtration and then washed in succession with hot xylene mixture and with methanol. Drying in a vacuum furnace at about 100° C. affords 0.400 g of the compound of the formula

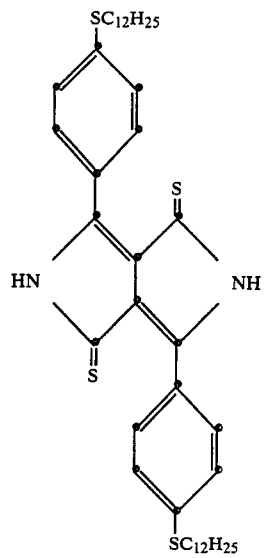

as dark blue powder. Melting point: 287°-289° C. (decomp.).

Analysis: C=69.3%; N=3.82%; H=8.33%; S=17.8%.

EXAMPLE 7

Under argon, a 100 ml sulfonating flask equipped with propeller mixer, thermometer and reflux condenser is charged with 1.45 g of 1,4-diketo-3,6-di(4-pyridyl)pyrrolo[3,4-c]pyrrole, 2.48 g of Lawesson's reagent and 30 ml of dimethylthioformamide. The mixture is heated to 110° C. and kept at this temperature for 3 hours. The reaction mixture is then cooled to 40° C. The unreacted starting pigment is removed by filtration, and the resultant product is precipitated in the mother liquor with acetone. The product is subsequently isolated by filtration at room temperature, washed with acetone and methanol and dried at 100° C. in a vacuum furnace, affording 440 mg of a dark blue product of the formula

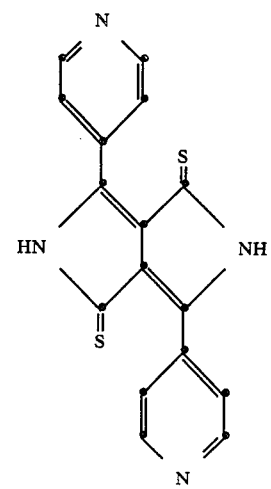

Melting point: >300° C. (decomp.).

EXAMPLE 8

0.54 g of the pigment obtained in accordance with Example 1 is dispersed in 14.4 g of a solution consisting of 7.5% by weight of Lucite ® 41 (a polymethyl methacrylate, manufactured by DuPont) in methyl ethyl ketone with 70 g of glass beads of 4-5 mm diameter in a 50 ml flask for 16 hours in a vibrator ball mill (type Vibratom ® of the Siebtechnick company in Mühlheim/Ruhr, West Germany). After removal of the glass beads, the pigment dispersion is spread with a drawing rod of nominally 150 μm wet film thickness onto an aluminium support. After drying, a layer is obtained which is of about 15 μm thickness and has electrophotographic properties (E½: about 10 μJ/cm²).

EXAMPLE 9

The procedure of Example 8 is repeated, but using in place of the pigment of Example 1 the pigment of Example 6. A layer with good electrophotographic properties is obtained.

EXAMPLE 10

0.3 g of the pigment of Example 1 is taken up in a mixture of 10 g of ethanol and methyl ethyl ketone (2:1 by volume), containing 0.2 g of ethyl cellulose. The suspension is then ground for 5 hours with glass beads and subsequently applied with a drawing rod to an aluminium plate (=charge generating layer). This layer is dried at 50° C. for 3 hours. The layer thickness is 6 μm. A second layer, consisting of a mixture of 0.6 g of the hydrazone of formula (5)

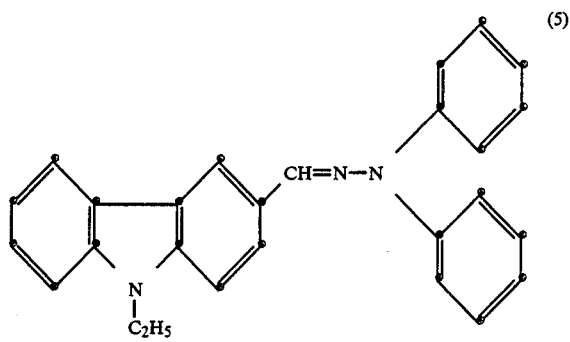

(5)

and 0.9 g of Lucite ® in 11 g of methyl ethyl ketone is then applied and dried at 50° C. for 15 hours. This photoreceptor exhibits a sensitivity (E½) of 5 μJ/cm² and the rechargeability is 430 volts.

EXAMPLE 11

The pigment of Example 1 is vaporised onto an aluminium support at a rate of 5 Å/sec under a vacuum of $10^{-6}$ mbar. The resultant layer thickness is 2000 to 3000 Å. This film is exposed to methanol vapour for 1 hour at room temperature. A second layer of the same composition as that in Example 10 is subsequently applied. The film exhibits absorption at 830 nm.

EXAMPLE 12

In accordance with the procedure of Example 11, the pigment of Example 6 is vaporised onto a support and the resultant film is exposed to acetone vapour for 1 hour. A second layer of the same composition of that in Example 10 is applied. The film exhibits absorption at 830 nm.

EXAMPLE 13

0.4 g of the pigment of Example 1 is ground for 2 days in 10 ml of distilled water with 40 g of glass beads of 1 mm diameter. The resultant product is isolated by filtration, dried at 50° C. for 24 hours, subsequently impregnated in ethyl acetate for 1 hour, and once more isolated by filtration and dried. The monolayer is prepared as described in Example 8. The film exhibits absorption at 830 nm.

EXAMPLE 14

By following the procedure of Example 10, a double layer can be produced by employing the pigment of Example 1 pretreated in the manner described in Example 13.

EXAMPLE 15

By following the procedure of Example 10, a double layer can be produced by employing the pigment of Example 6 pretreated in the manner described in Example 13.

What is claimed is:
1. A compound of formula (1)

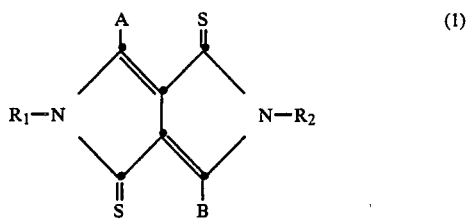

(1)

wherein A and B are pyridyl or where A and B are identical or different radicals of formula (3)

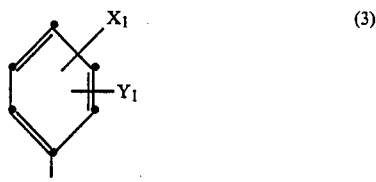

(3)

wherein one of the substituents $X_1$ and $Y_1$ is a hydrogen, chlorine or bromine atom, a methyl, cyano, N,N-dimethylamino, N,N,diethylamino, $C_1$-$C_{12}$alkoxy, $C_1$-$C_{12}$alkylmercapto or $C_2$-$C_4$alkoxycarbonyl group, and the other substitutent is a hydrogen atom, and
$R_1$ and $R_2$ are hydrogen or alkyl of 1 to 12 carbon atoms.

2. A compound according to claim 1, wherein A and B are identical or different radicals of formula (3)

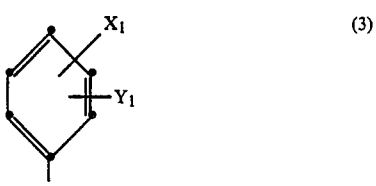

(3)

wherein one of the substituents $X_1$ and $Y_1$ is a hydrogen, chlorine or bromine atom, a methyl, cyano, N,N-dimethylamino, N,N,diethylamino, $C_1$-$C_{12}$alkoxy, $C_1$-$C_{12}$alkylmercapto or $C_2$-$C_4$alkoxycarbonyl group, and the other substitutent is a hydrogen atom.

3. A compound according to claim 1, wherein the substituents $X_1$ and $Y_1$ are in meta- or p-position to the dithioketopyrrolopyrrole group.

4. The compound which is 1,4-dithiono-3-phenyl-6-(3,4,5-trimethoxyphenyl)pyrrolo[3,4-c]pyrrole.

* * * * *